United States Patent
Dash et al.

(10) Patent No.: US 9,422,316 B2
(45) Date of Patent: Aug. 23, 2016

(54) METHOD OF PREPARING HALOGENATED SILAHYDROCARBYLENES

(71) Applicant: Dow Corning Corporation, Midland, MI (US)

(72) Inventors: Aswini K. Dash, Midland, MI (US); Dimitris Elias Katsoulis, Midland, MI (US); Matthew J. McLaughlin, Midland, MI (US); Wendy Sparschu, Bay City, MI (US)

(73) Assignee: DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 14/436,095

(22) PCT Filed: Jul. 2, 2013

(86) PCT No.: PCT/US2013/049032
§ 371 (c)(1),
(2) Date: Apr. 16, 2015

(87) PCT Pub. No.: WO2014/062255
PCT Pub. Date: Apr. 24, 2014

(65) Prior Publication Data
US 2015/0232488 A1 Aug. 20, 2015

Related U.S. Application Data

(60) Provisional application No. 61/714,336, filed on Oct. 16, 2012.

(51) Int. Cl.
*C07F 7/08* (2006.01)
*C07F 7/16* (2006.01)
*C08G 77/60* (2006.01)

(52) U.S. Cl.
CPC .. *C07F 7/16* (2013.01); *C08G 77/60* (2013.01)

(58) Field of Classification Search
CPC .................................. C07F 7/16; C08G 77/60
USPC ........................................................ 556/477
See application file for complete search history.

(56) References Cited

U.S. PATENT DOCUMENTS

| | | | |
|---|---|---|---|
| 2,380,996 A | 8/1945 | Rochow et al. | |
| 2,381,000 A | 8/1945 | Patnode et al. | |
| 2,381,002 A | 8/1945 | Patnode et al. | |
| 2,403,370 A | 7/1946 | Hurd | |
| 2,888,476 A | 5/1959 | Little | |
| 3,057,686 A | 10/1962 | Muetterties et al. | |
| 4,314,908 A | 2/1982 | Downing et al. | |
| 4,526,769 A | 7/1985 | Ingle et al. | |
| 4,836,997 A | 6/1989 | Lepage et al. | |
| 4,888,435 A | 12/1989 | Chadwick et al. | |
| 4,946,980 A | 8/1990 | Halm et al. | |
| 4,973,725 A | 11/1990 | Lewis et al. | |
| 5,175,329 A | 12/1992 | Bokerman et al. | |
| 5,473,037 A | 12/1995 | Itoh et al. | |
| 6,156,380 A | 12/2000 | Aramata et al. | |
| 6,790,749 B2 | 9/2004 | Takemura et al. | |
| 6,887,448 B2 | 5/2005 | Block et al. | |
| 7,212,778 B2 | 5/2007 | Hisakuni | |
| 7,223,879 B2 | 5/2007 | Buchwald et al. | |
| 7,355,060 B2 | 4/2008 | Ogawa et al. | |
| 7,442,824 B2 | 10/2008 | Paetzold et al. | |
| 7,559,969 B2 | 7/2009 | Sanjurjo et al. | |
| 7,716,590 B1 | 5/2010 | Nathan | |
| 7,728,176 B2 | 6/2010 | Masaoka et al. | |
| 8,124,809 B2 | 2/2012 | Masaoka et al. | |
| 8,519,207 B2 | 8/2013 | Armbruester et al. | |
| 8,604,249 B2 | 12/2013 | Masaoka et al. | |
| 8,674,129 B2 | 3/2014 | Dash et al. | |
| 8,697,900 B2 | 4/2014 | Anderson et al. | |
| 8,772,525 B2 | 7/2014 | Katsoulis et al. | |
| 2005/0074387 A1 | 4/2005 | Bulan et al. | |
| 2006/0165580 A1 | 7/2006 | Lipshutz | |
| 2014/0212352 A1 | 7/2014 | Onal et al. | |
| 2014/0256975 A1 | 9/2014 | Katsoulis et al. | |

FOREIGN PATENT DOCUMENTS

DE 3024319 1/1982
DE 4041644 6/1992

(Continued)

OTHER PUBLICATIONS

International Search Report; PCT/US2013/049032.*
Beccalli, Egle M., et al., C—C, C—O, C—N Bond Formation on sp2 Carbon by Palladium(II)-Catayzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.
Dallas T. Hurd, The Vapor Phase Alkylation and Hydrogenation of Chlorosilanes, J. Am. Chem. Soc., 1945, 67 (9), pp. 1545-1548.
Ding, et al., CuCl-Catalyzed Hydrogenation of Silicon Tetrachloride in the Presence of Silicon: Mechanism and Kinetic Modeling, Ind. Eng. Chem. Res.

(Continued)

*Primary Examiner* — Porfirio Nazario Gonzalez
*Assistant Examiner* — Kofi Adzamli
(74) *Attorney, Agent, or Firm* — Matthew T. Fewkes

(57) ABSTRACT

A method comprises separate and consecutive steps (i) and (ii). Step (i) includes contacting a copper catalyst with hydrogen gas and a halogenated silane monomer at a temperature of 500° C. to 1400° C. to form a silicon-containing copper catalyst comprising at least 0.1% (w/w) of silicon. Step (ii) includes contacting the silicon-containing copper catalyst with an organohalide at a temperature of 100° C. to 600° C. to form a reaction product. The organohalide has formula $H_aC_bX_c$, where X is a halogen atom, subscript a is an integer of 0 or more, subscript b is an integer of 1 or more, and subscript c is an integer of 2 or more. The method produces a reaction product. The reaction product includes a halogenated silahydrocarbylene.

15 Claims, No Drawings

(56) References Cited

FOREIGN PATENT DOCUMENTS

| DE | 19654154 | 6/1997 | | |
|---|---|---|---|---|
| GB | 2112407 | 7/1983 | | |
| JP | 197623226 | 2/1976 | | |
| JP | 2009111202 | 5/2009 | | |
| WO | 9727239 | 7/1997 | | |
| WO | WO 2011149588 A1 | * 12/2011 | ............. | C07F 7/122 |
| WO | 2014028417 | 2/2014 | | |

OTHER PUBLICATIONS

Eaborn, C. et al., Further studies on reactions of organic halides with disilanes catalysed by transition metal complexes, Journal of Organometallic Chemistry, vol. 225, 1982, pp. 331-341.

Fritz, G. et al.; Synthesis of organosilicon compounds. XI, Formation of silicon methylene compounds from dichloromethane and silicon, Zeitschrift fuer Anorganische und Allgemeine Chemie (1960), 306, 39-47.

Golubtsov, S.A. et al., Role of the Products of Partial Chlorination of Silicon in the Formation of Methyltrichlorosilane, Russian Chemical Bulletin, vol. 21, No. 3 (1972), pp. 584-586.

H. Walter, Mechanism of the silicide-catalysed hydrodehalogenation of silicon tetrachloride to trichlorosilane, J. Chem. Soc., Faraday Trans., 1996,92, 4605-4608.

Han, Joon Soo, et al.; Direct Synthesis of Tris(chlorosilyl)methanes Containing Si—H Bonds, Organometallics (1997), 16(1), 93-96.

Juszczyk et al. of Pd/SiO2 catalysts during high temperature reduction., Department of Catalysis on Metals, Institute of Physical Chemistry, Polish Academy of Sciences, Warsaw, Pol. Catalysis Letters (2002), 78(1-4), 95-98.

Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.

Lobusevich, N.P. et al,, Reactions During Direct Synthesis of Alkylchlorosilanes., vol. 48, No. 11, 1978, pp. 2534-2541. (Abstract).

Methivier, et al., Pd/SiC catalysts. Characterization and catalytic activity for the methane total oxidation.. Institut de Recherches sur la Catalyse—CNRS, conventionne a l'Universite Claude Bernard Lyon 1, Villeurbanne, Fr. Journal of Catalysis (1998), 173(2), 374-382.

Moreno-Manes, Marcial et al., Formation of Carbon—Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.

Mulla, et. al., "Reaction of Magnesium Silicide & Silicon Tetrachloride/Trichlorosilane in Presence of Hydrogen", Indian Journal of Chemistry, Sep. 1988, pp. 756-758, vol. 27A.

Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12), 1841-1848.

Tanaka, Miyoko et al., Nanomaterials Laboratory National Institute for Materials Science, Tsukuba, Sakura, Japan, Journal of Crystal Growth (2002), 237-239(Pt. 1), 254-258.

Terao, Jun et al., Transition metal-catalyzed C—C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro—Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon—carbon coupling reactions catalyzed by heterogeneous palladium catalysts., Institute fuer Chemie, Humboldt—Universitaet Berlin, Berlin, Germany. Chemical Reviews (Washington, DC, United States) (2007), 107(1), 133-173.

Seung Ho Yeon et al., Effects of hydrogen chloride addition to the direct reaction of methylene chloride with elemental silicon, Journal of Organometallic Chemistry, 1996, 516, p. 91-95.

* cited by examiner

METHOD OF PREPARING HALOGENATED SILAHYDROCARBYLENES

CROSS REFERENCE TO RELATED APPLICATIONS

This application is a U.S. national stage filing under 35 U.S.C. §371 of PCT Application No. PCT/US13/049032 filed on 2 Jul. 2013, currently pending, which claims the benefit of U.S. Provisional Patent Application No. 61/714,336 filed 16 Oct. 2012 under 35 U.S.C. §119 (e). PCT Application No. PCT/US13/049032 and U.S. Provisional Patent Application No. 61/714,336 are hereby incorporated by reference.

Halogenated silahydrocarbylenes are useful in the silicones industry as raw materials for products such as silicone resins. There is a need in the industry to provide methods for preparing halogenated silahydrocarbylenes.

SUMMARY OF THE INVENTION

A method of preparing a reaction product comprising a halogenated silahydrocarbylene, comprises two separate and consecutive steps. The first step (i) includes contacting a copper catalyst with hydrogen ($H_2$) gas and a halogenated silane monomer at a temperature of 500° C. to 1400° C. to form a silicon-containing copper catalyst comprising at least 0.1% (w/w) of silicon. The second step (ii) includes contacting the silicon-containing copper catalyst with an organohalide at a temperature of 100° C. to 600° C. to form a reaction product comprising a halogenated silahydrocarbylene.

The halogenated silane monomer used in step (i) of this method includes a silicon tetrahalide, a trihalosilane, or a combination thereof. The copper catalyst used in step (i) of this method comprises copper. The organohalide used in step (ii) of the method has formula $H_aC_bX_c$, where X is a halogen atom, subscript a is an integer of 0 or more, subscript b is an integer of 1 or more, and subscript c is an integer of 2 or more.

DETAILED DESCRIPTION OF THE INVENTION

Unless otherwise indicated by the context of the specification, all amounts, ratios, and percentages are by weight, and the articles 'a', 'an', and 'the' each refer to one or more. In this application, 'Me' represents a methyl group, 'Et' represents an ethyl group, 'Pr' represents a propyl group and includes n-propyl and iso-propyl, and 'Bu' represents a butyl group and includes n-butyl, tert-butyl, iso-butyl, and sec-butyl.

A method comprises separate and consecutive steps (i) and (ii). Step (i) comprises contacting a copper catalyst with hydrogen gas and a halogenated silane monomer comprising a silicon tetrahalide, a trihalosilane, or combination thereof, at a temperature of 500° C. to 1400° C. to form a silicon-containing copper catalyst comprising at least 0.1% (w/w) of silicon. Step (ii) comprises contacting the silicon-containing copper catalyst with an organohalide at a temperature of 100° C. to 600° C. to form a reaction product, where the organohalide has formula $H_aC_bX_c$, where X is a halogen atom, subscript a is an integer of 0 or more, subscript b is an integer of 1 or more, and subscript c is an integer of 2 or more. The reaction product comprises a halogenated silahydrocarbylene. The reaction product may further comprise a halohydrocarbylene and/or a halosilane.

The copper catalyst in step (i) comprises copper. The copper catalyst may optionally further comprise at least one element selected from calcium, cesium, gold, magnesium, nickel, sulfur, tin, and zinc. Alternatively, in addition to copper, the copper catalyst may further comprise at least one element selected from calcium, cesium, gold, magnesium, sulfur, tin, and zinc. Alternatively, the copper catalyst may be a mixture of copper, gold, and magnesium. One skilled in the art will understand that the copper catalyst may include impurities or various amounts of other metal or non-metal elements, including but not limited to silicon, without exceeding the scope of the present disclosure. For example, the copper catalyst may be a silicon-containing catalyst previously exposed to step (ii) that is being regenerated according to an optional third process step (iii) as described hereafter or the catalyst may be derived from a metal silicide, including but not limited to a copper silicide. The copper catalyst may optionally include a metal oxide or carbon-based support; alternatively an activated carbon support, i.e., the copper catalyst can be a supported catalyst or an unsupported catalyst. Examples of supports include, but are not limited to, oxides of aluminum, cerium, titanium, zirconium, and silicon; and carbon supports such as activated carbon, carbon nanotubes, fullerenes, and other allotropic forms of carbon. Alternatively, the support may be activated carbon.

The unsupported copper catalyst may comprise 0.1% to 100% (w/w) of copper, based on the total weight of the catalyst. Alternatively, the unsupported copper catalyst may comprise 0.1% to 80% (w/w); alternatively 1% to 80% (w/w); alternatively, 10% to 80% (w/w); alternatively, 40% to 80% (w/w) of copper based on the total weight of the catalyst.

When the copper catalyst includes a support, the catalyst may comprise 0.1% to less than 100% (w/w), alternatively 0.1% to about 80% (w/w); alternatively 0.1% to about 50% (w/w), alternatively 0.1% to about 35% (w/w), of copper (or the combination of copper and the at least one element selected from calcium, cesium, gold, magnesium, nickel, sulfur, tin, and zinc, when said at least one element is present), based on the combined weight of the support and copper (or the combined weight of the support, copper and the at least one element).

The copper catalyst can take any physical form including, but not limited to, lumps, granules, flakes, powder, nanoparticles, nano-wires, and mesh. Several specific examples of unsupported copper catalysts include, but are not limited to, metallic copper; copper chloride, copper oxide, mixtures of metallic copper and metallic nickel; mixtures of metallic copper and metallic gold; mixtures of metallic copper, metallic gold and magnesium chloride; mixtures of metallic copper, metallic gold and sulfur; mixtures of metallic copper and tin; mixtures of metallic copper and cesium; and mixtures of metallic copper and calcium chloride. As used herein, the term "metallic" means that the metal has an oxidation number of zero. Several specific examples of supported copper catalysts include, but are not limited to, the unsupported copper catalysts described above dispersed within, and/or reduced on, an activated carbon support.

The unsupported and supported copper catalysts useful herein can be made by any convenient process. For example, one process of making the unsupported catalyst includes mixing the copper and the at least one element selected from calcium, cesium, gold, magnesium, nickel, sulfur, tin, and zinc together to form the copper catalyst. Alternatively, metal salts including, but not limited to, halide, acetate, nitrate, and carboxylate salts, may be first mixed in predetermined or desired proportions and then be subsequently subjected to a known reduction process. One such reduction process is described below as a specific example, among others to demonstrate the preparation of a supported copper catalyst. This process may leave some salts, such as magnesium chloride, unreduced, while reducing others.

The supported copper catalyst may be prepared by, for example, combining a copper salt, such as cupric chloride, in a solvent, such as water or acid, applying the mixture to a support, and reducing the copper salt on the surface of the support. For example, $CuCl_2$ can be dissolved in water or hydrochloric acid and mixed with activated carbon. Excess $CuCl_2$ solution can then be removed, and the activated carbon-$CuCl_2$ mixture dried. The $CuCl_2$ can then be reduced on the activated carbon support with hydrogen at 500° C. to give a supported copper catalyst. The steps of adding the metallic salts followed by subsequent reduction can each be carried out as a single step or involve a multiple step process without exceeding the scope of the present disclosure. Additional examples of making unsupported and supported copper catalysts are provided in the examples described herein, as well as in co-pending International Patent Publication No. WO2011/149588, as filed on Mar. 31, 2011, the entire contents of which are hereby incorporated by reference.

The halogenated silane monomer comprises $HSiX_3$, or $SiX_4$, or a combination thereof, where each X is independently Br, Cl, F, or I; alternatively Cl. Alternatively, the halogenated silane monomer may comprise a combination comprising $SiX_4$ and $HSiX_3$, where X is as defined above. Several examples of halogenated silane monomers include, but are not limited to silicon tetrachloride, silicon tetrabromide, silicon tetraiodide, silicon tetrafluoride, trichlorosilane, tribromosilane, or mixtures thereof. Alternatively the silicon tetrahalide is silicon tetrachloride. The mole ratio of hydrogen to the halogenated silane monomer used to contact the copper catalyst ranges from 10,000:1 to 0.01:1, alternatively 100:1 to 0.1:1, alternatively 20:1 to 1:1, alternatively 15:1 to 1:1, and alternatively 10:1 to 1:1.

The reactor system used in the first step (i) of the method may include any reactor that is suitable for combining and reacting a gas with a solid material. For example, suitable reactor configurations include, but are not limited to, a packed bed, a stirred bed, a vibrating bed, a moving bed, a re-circulating bed, or a fluidized bed. When using a re-circulating bed, the silicon-containing copper catalyst can be circulated from a first bed used to perform step (i) to a second bed used to perform step (ii).

When desirable to facilitate or control the reaction, the reactor system may include a means to control the temperature of the reaction. The temperature at which the hydrogen gas and halogenated silane monomer make contact with the copper catalyst can range from 500° C. to 1400° C.; alternatively 500° C. to 1200° C.; alternatively 500° C. to 950° C. The pressure at which the hydrogen gas and halogenated silane monomer make contact with the copper catalyst can be sub-atmospheric, atmospheric, or super-atmospheric. For example, the pressure may range from 0 to 2000 kilopascals gauge (kPag); alternatively from 0 to 1000 kPag; alternatively from 100 to 800 kPag, at a temperature from 500° C. to 1400° C. The hydrogen gas and halogenated silane monomer may be fed into the reactor simultaneously; however, other methods of combining, such as by separate pulses, are also within the scope of the method. The hydrogen gas and halogenated silane monomer may be mixed together before being fed into the reactor (e.g., through one feed inlet, or alternatively, the mixture may be fed through more than one feed inlet). Alternatively, the hydrogen and the halogenated silane monomer may be fed into the reactor separately (e.g., each gas may be fed through a different feed inlet).

The residence time for copper catalyst to be in contact with the hydrogen and halogenated silane monomer is predetermined such that it is sufficient to form the silicon-containing copper catalyst. For example, a sufficient residence time for the copper catalyst to be in contact with the hydrogen and silicon tetrahalide is typically at least 0.01 seconds; alternatively at least 0.1 seconds; alternatively 0.1 seconds to 5 hours; alternatively from 0.1 seconds to 45 minutes; alternatively from 0.1 seconds to 5 minutes. Alternatively, there is no upper limit on the residence time for which step (i) is conducted. As used herein, "residence time" of step (i) means the time during which one reactor volume of copper catalyst makes contact with the hydrogen and halogenated silane monomer as copper catalyst passes through the reactor system in a continuous process or during which copper catalyst is placed within the reactor in a batch process. The desired residence time may be achieved by adjusting the copper catalyst flow rate in a continuous process or the duration of the step in a batch process.

The copper catalyst as used in step (i) of the method is present in a sufficient amount. As used herein, a "sufficient amount" of copper catalyst means enough catalyst to form the silicon-containing copper catalyst, as described below, when the hydrogen and halogenated silane monomer make contact with the copper catalyst. For example, a sufficient amount of catalyst is at least 0.01 mg catalyst/$cm^3$ of the volume in the reactor system; alternatively at least 0.5 mg catalyst/$cm^3$ of the reactor volume; alternatively from 1 to 10,000 mg catalyst/$cm^3$ of the reactor volume.

The silicon-containing copper catalyst comprises at least 0.1% (w/w), alternatively 0.1% to 90% (w/w), alternatively 0.1% to 55% (w/w), alternatively 1% to 20% (w/w), and alternatively 1% to 5% (w/w), of silicon based on the total weight of silicon-containing copper catalyst, including any support (if present). The percentage of silicon in the silicon-containing copper catalyst can be determined using standard analytical tests. For example, the percentage of silicon may be determined using inductively coupled plasma atomic emission spectroscopy (ICP-AES) and ICP mass spectrometry (ICP-MS).

In the second step (ii) of the method, the silicon-containing copper catalyst makes contact with an organohalide at a temperature of 100° C. to 600° C. to form the reaction product comprising the halogenated silahydrocarbylene. The organohalide in step (ii) has formula $H_aC_bX_c$, where subscript a represents average number of hydrogen atoms present, subscript b represents average number of carbon atoms present, and subscript c represents average number of halogen atoms present. Subscript a is an integer of 0 or more, subscript b is an integer of 1 or more, and subscript c is an integer of 2 or more. When the organohalide is a noncyclic alkyl halide, then a quantity (a+c)=a quantity (2b+2). When the organohalide is a monocyclic cycloalkyl halide, then the quantity (a+c)=2b. Each X is independently selected from Br, Cl, F, and I; alternatively each X is Cl. Examples of suitable organohalides include, but are not limited to, methylene chloride ($H_2CCl_2$), $HCCl_3$, and $CCl_4$.

The reactor systems suitable for use in step (ii) are similar to or the same as the reactor systems previously described for use in step (i). The same reactor system may be used for step (i) as used in step (ii); however, separate or different reactor systems may alternatively be used without exceeding the scope of the present disclosure. In such a reactor system, the organohalide typically makes contact with the silicon-containing copper catalyst by feeding the organohalide into the reactor that contains the silicon-containing copper catalyst produced in step (i). The temperature at which the organohalide makes contact with the silicon-containing copper catalyst may range from 100° C. to 600° C., alternatively 200° C. to 500° C., and alternatively 250° C. to 375° C.

The residence time of the organohalide being in contact with the silicon-containing copper catalyst is sufficient for the organohalide to react with the silicon-containing copper catalyst to form the reaction product comprising the halogenated silahydrocarbylene. The residence time for silicon-containing copper catalyst to be in contact with the organohalide may be at least 1 minute; alternatively at least 5 minutes; alternatively 1 minute to 120 minutes; alternatively 5 minutes to 90 minutes; and alternatively 5 minutes to 60 minutes. Alternatively, there is no upper limit on the residence time for which step (ii) is performed. As used herein, "residence time" of step (ii) means the time in which one reactor volume of silicon-containing copper catalyst makes contact with the organohalide as this gas passes through the reactor system in a continuous process or that is placed within the reactor in a batch process. The desired residence time can be achieved by adjusting the flow rate of the organohalide or the duration of the step in a batch process.

The pressure at which the organohalide makes contact with the silicon-containing copper catalyst in step (ii) can be sub-atmospheric, atmospheric, or super-atmospheric. For example, the pressure may range from 0 to 2000 kPag, alternatively from 100 to 2000 kPag, alternatively from 100 to 1000 kPag, and alternatively from 100 to 800 kPag.

The silicon-containing copper catalyst used in step (ii) of the method is present in a "sufficient amount for step (ii)". As used herein, a "sufficient amount for step (ii)" of silicon-containing copper catalyst is enough catalyst to form the halogenated silahydrocarbylene, described below, when contacted with the organohalide. For example, a sufficient amount of silicon-containing copper catalyst is at least 0.01 mg catalyst/cm$^3$ of reactor volume; alternatively at least 0.5 mg catalyst/cm3 of reactor volume; alternatively from 1 to 10000 mg catalyst/cm3 of reactor volume.

Step (ii) is typically conducted until the silicon in the silicon-containing copper catalyst is spent, e.g., falls below a predetermined limit. The predetermined limit for the amount of silicon in the silicon-containing catalyst at which step (ii) is halted or suspended is typically less than 100% (w/w); alternatively, 90% (w/w) or less, alternatively less than 75% (w/w), and alternatively less than 40% (w/w), of its initial weight percent, based on the total weight of catalyst including any support. As used herein, the "initial weight percent of silicon in the silicon-containing copper catalyst" means the weight percent of silicon in the silicon-containing copper catalyst before the silicon-containing copper catalyst is contacted with the organohalide in step (ii). The amount of silicon in the silicon-containing copper catalyst can be monitored by correlating reaction product production or alternatively, halogenated silahydrocarbylene production, with the weight percent of silicon in the silicon-containing copper catalyst and then monitoring halogenated silahydrocarbylene production or it may be determined as described above for the silicon-containing copper catalyst.

Step (i) and step (ii) of the method are conducted separately and consecutively. As used herein, "separately" means that the step (i) and step (ii) do not overlap or coincide. As used herein, "consecutively" means that step (ii) is performed after step (i) in the method; however, additional steps may be performed between steps (i) and (ii), and/or after step (ii) such as described below.

The method may optionally further comprise a third step (iii) that occurs after step (ii) is suspended or halted. This third step (iii) involves repeating the first step (i) and second step (ii) one or more times. Upon repeating the first step (i), the spent silicon-containing copper catalyst from step (ii) is contacted with the mixture comprising hydrogen gas and halogenated silane monomer at a temperature of 500° C. to 1400° C. to reform the silicon-containing copper catalyst comprising at least 0.1% (w/w) silicon. This reformed silicon-containing copper catalyst is then subjected to repeating the second step (ii) by making contact with the organohalide at a temperature of 100° C. to 600° C. to form a reaction product, or alternatively a halogenated silahydrocarbylene. This third step (iii) may be performed at least 1 time, alternatively from 1 to 10$^5$ times, alternatively from 1 to 1000 times, alternatively from 1 to 100 times, alternatively from 1 to 10 times. Alternatively, this third step (iii) may be performed more than 1 time with no upper limit being placed on the number of times step (iii) may be performed without exceeding the scope of the disclosure; alternatively, the upper limit may be determined according to commercial viability.

The method may optionally further comprise an intermediate step of purging the reactor system before contacting the silicon-containing copper catalyst with the organohalide in the second step (ii). This intermediate purging step may occur between step (i) and step (ii) either in conjunction with the initial performance of the first step (i) and second step (ii) or upon repeating these two steps (i) and (ii) as part of the third step (iii). As used herein, "purging" means to introduce a gas stream to the reactor containing the silicon-containing copper catalyst to remove unwanted materials. Unwanted materials may include, for example, $H_2$, $O_2$, and $H_2O$, among others. Purging may be accomplished with an inert gas, such as argon, or with a reactive gas, such as hydrogen, or both. Alternatively, purging may be performed first with a reactive gas and thereafter with an inert gas. Alternatively, purging may be performed first with an inert gas and thereafter with a reactive gas.

If the organohalide or halogenated silane monomer are liquids at or below standard temperature and pressure, the method may further comprise pre-heating and gasifying the organohalide or halogenated silane monomers by any known method prior to contacting the halogenated silane monomer with the copper catalyst in step (i) or contacting the organohalide with the silicon-containing copper catalyst in step (ii). Alternatively, the process may further comprise bubbling the hydrogen gas through the liquid halogenated silane monomer or organohalide in order to vaporize the halogenated silane monomers or organohalide prior to making contact with the copper catalyst in step (i) and the silicon-containing copper catalyst in step (ii), respectively.

The method may optionally further comprise a fourth step (iv) of recovering the reaction product produced in step (ii). The reaction product may be recovered by, for example, removing gaseous halogenated organosilicon compound from the reactor system followed by isolation via distillation. According to one aspect of the present disclosure, the reaction product produced by the method described and exemplified above comprises a halogenated silahydrocarbylene. Halogenated silahydrocarbylenes may have formula $X_dH_eR^1_fSi$—R—$SiX_dH_eR^1_f$, where each X is independently a halogen atom as described above, each subscript d is independently 0, 1, 2, or 3; each subscript e is independently 0, 1, or 2, each subscript f is independently 0, 1, or 2, with the proviso that a quantity (d+e+f)=3, and with the proviso that at least one instance of d>0, each $R^1$ is independently a monovalent hydrocarbon group, such as an alkyl group of 1 to 10 carbon atoms or a cycloalkyl group of 4 to 10 carbon atoms, and R is a divalent hydrocarbon group, such as an alkylene group of 1 to 10 carbon atoms or a cycloalkylene group of 4 to 10 carbon atoms. Alternatively, subscript d may be 2 or 3. Alternatively, subscript e may be 0. Alternatively, subscript f may be 0 or 1. Alternatively, each X may be Cl. Alternatively, R may be an alkylene group such as methylene or ethylene; alternatively methylene. Alternatively, $R^1$, may be an alkyl group selected from Me, Et, Pr, and Bu; alternatively Me and Et.

The method may also produce other products in addition to the halogenated silahydrocarbylenes. For example, a second product produced by the method may comprise a halohydrocarbylene such as haloalkylene. Exemplary haloalkylenes include chloromethylene and chloroethylene. The method may alternatively produce a halosilane, such as a chlorosilane, in addition to, or instead of the haloalkylene.

The method may optionally further comprise an additional step (v) of reacting the halogenated silahydrocarbylene recovered in step (iv) to produce resins for subsequent use in a variety of industries and applications. Such reaction may be accomplished using any method or process known in the art capable of producing the desired resin.

EXAMPLES

The following examples are presented to illustrate the method of the present invention, but are not to be considered as limiting the invention, which is set forth in the claims. Table 1 lists several abbreviations used to indicate the identified terms throughout the following examples. The reaction system, reagents, product analysis, and flow rates used throughout the Examples are also summarized below.

The reaction apparatus comprised a 4.8 mm inner diameter quartz glass tube in a flow reactor. The reactor tube was heated using a Lindberg/Blue Minimite 2.54 cm tube furnace. $H_2$ delivered via Brooks Delta mass flow controller and Ar delivered via Omega FMA 5500 mass flow controller. A stainless steel $SiCl_4$ bubbler was used to introduce $SiCl_4$ into the $H_2$ gas stream. The amount of $SiCl_4$ in the $H_2$ gas stream was adjusted by changing the temperature of the $SiCl_4$ in the bubbler according to calculations using well known thermodynamic principles. The reactor effluent passed through an actuated 6-way valve from Vici.

The activated carbon, $AuCl_3$, $MgCl_2$ were purchased from Sigma Aldrich, Inc. of St. Louis, Mo., U.S.A. The $CuCl_2$-$2H_2O$ was purchased from Alfa Aesar of Ward Hill, Mass., U.S.A.

The effluent of the reactor containing the products and byproducts was passed through an actuated 6-way valve (Vici) with constant 100 uL injection loop before being discarded. Samples were taken from the reaction stream by actuating the injection valve and the 100 uL sample passed directly into the injection port of a 7890A Agilent GC-MS for analysis with a split ratio at the injection port of 100:1. The GC contained one Restek DCA column used and connected only to a mass spectrometer (Agilent 7895C MSD) for sensitive detection of trace products and positive identification of any products that formed. The column was heated by the GC oven.

Flow rate ratios were determined using known thermodynamic principles with the flow rates, at standard temperature and pressure, of Hydrogen, Argon, $SiCl_4$, $CH_2Cl_2$, $CHCl_3$, and $CCl_4$.

TABLE 1

List of abbreviations and terms used herein.

| Abbreviation | Word | Abbreviation | Word |
|---|---|---|---|
| g | gram | mL | Milliliter |
| mg | milligram | cm | Centimeter |
| w/w | weight ratio | sccm | standard cubic centimeters per minute |
| mol | mole | GC | gas chromatograph |
| min | minute | GC-MS | gas chromatograph-mass spectrometer |
| ° C. | degrees Celsius | H2 | Hydrogen |
| N/A | not applicable | Ar | Argon |

Example 1

Method of Producing Copper Catalyst Comprising Cu, Au, and Mg

The following ingredients, $CuCl_2$-$2H_2O$ (99±%, 5.315 g), 0.139 g $AuCl_3$ (99%), and 0.163 g $MgCl_2$-$6H_2O$ (99.995%) were dissolved in deionized $H_2O$ to form a metal salt mixture. This metal salt mixture was then added to 4.330 g of activated carbon. Excess liquid not absorbed by the activated carbon was dabbed away, and then the activated carbon was dried at 90° C. for 15 hours. The dried activated carbon had a final dry weight of 8,224 g. Based on the starting weight of the activated carbon and metal solution loading, the metal loading on the activated carbon was calculated to be 23.7% (w/w) Cu, 1.1%, (w/w) Au, and 0.5% (w/w) Mg. The metal loaded activated carbon (0.75 g) was charged into a quartz glass tube and placed into a flow reactor. Activation and reduction of catalyst was performed by flowing $H_2$ at 100 sccm (controlled via Brooks Delta mass flow controller) into the glass tube containing the catalyst in the reactor at 600° C. for 2 hours. The heating was accomplished using a Lindberg/Blue Minimite 2.54 cm tube furnace.

Example 2

$CH_2Cl_2$ with Ar

Copper catalyst (0.75 g) comprising an activated carbon supported mixture of copper, gold, and magnesium, prepared as described above in example 1, was treated in $H_2$/$SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the glass tube of a flow reactor containing the copper catalyst to form a silicon-containing copper catalyst. After 30 minutes the $SiCl_4$ flow was ceased and a hydrogen flow of 100 sccm was maintained while cooling to 300° C. over a period of 1 hour. When the reactor reached 300° C., all $H_2$ was purged from the reactor and catalyst with an argon flow of 50 sccm for 30 min. After the 30 min, the argon flow was ceased, and Ar was fed at a flow rate of 5 sccm through a bubbler containing $CH_2Cl_2$ and into the reactor at 300° C., and atmospheric pressure. The reaction was periodically sampled and analyzed by GC/GC-MS as described above to determine the Si-containing species leaving the reactor. Next, the Ar/$CH_2Cl_2$ feed was ceased, and the silicon-containing copper catalyst was activated/regenerated with 100 sccm $H_2$ at 600° C. It was then contacted again with $H_2$/$SiCl_4$, to reform the silicon-containing copper catalyst, for 30 min at 750° C. The combined flow rate of $H_2$ and $SiCl_4$ was 109 sccm, and the mole ratio of $H_2$ to $SiCl_4$ was 11.25:1. After the silicon-containing copper catalyst was reformed, it was purged with argon again, and Ar/$CH_2Cl_2$ was contacted with the reformed silicon-containing copper catalyst as described above. This cycle was repeated once. The results are shown in Table 2. In Table 2, to calculate % in effluent, the peak areas were summed, and then each individual peak area was divided by the sum and multiplied by 100. This example demonstrates that chlorinated silamethylenes can be produced by the method of the invention and that the selectivity and production of chlorinated silamethylenes improves with subsequent cycles of catalyst regeneration and reaction.

TABLE 2

Production of halogenated silaalkylenes, chloroethylenes, and chlorosilanes when silicon-containing copper catalyst is reacted with Ar/CH$_2$Cl$_2$.

| Cycle 1 | | Cycle 2 | |
|---|---|---|---|
| Compound | % in Effluent | Compound | % in Effluent |
| Ar | 12.3 | Ar | 6.78 |
| MeCl | 2.92 | MeCl | 1.18 |
| HSiCl$_3$ | 10.31 | HSiCl$_3$ | 3.50 |
| CH$_2$Cl$_2$ | 23.29 | CH$_2$Cl$_2$ | 17.34 |
| SiCl$_4$ | 27.99 | SiCl$_4$ | 6.29 |
| MeSiCl$_3$ | 21.63 | MeSiCl$_3$ | 8.32 |
| Me$_2$SiCl$_2$ | 0.19 | EtSiCl3 | 0.35 |
| EtSiCl$_3$ | 0.65 | Cl$_2$HSiCH$_2$SiHCl$_2$ | 2.30 |
| Cl$_2$HSiCH$_2$SiCl$_3$ | 0.09 | Cl$_2$HSiCH$_2$SiCl$_3$ | 18.56 |
| Cl$_3$SiCH$_2$SiCl$_3$ | 0.62 | Cl$_2$HSiCH$_2$SiCl$_2$Me | 1.68 |
| | | Cl$_3$SiCH$_2$SiCl$_3$ | 27.94 |
| | | Cl$_2$MeSiCH$_2$SiCl$_3$ | 3.73 |
| | | Cl$_2$MeSiCH$_2$SiMeCl$_2$ | 0.40 |
| | | Cl$_3$Si(CH$_2$)$_2$SiCl3 | 1.62 |

Cycle 1 main products were SiCl$_4$ and MeSiCl$_3$.
Cycle 2 main products were Cl$_2$HSiCH$_2$SiCl$_3$ and Cl$_3$SiCH$_2$SiCl$_3$.

Example 3

CH$_2$Cl$_2$ with H$_2$

Copper catalyst (0.75 g) comprising an activated carbon supported mixture of copper, gold, and magnesium, prepared as described above in example 1, was treated in H$_2$/SiCl$_4$ for 30 min at 750° C. by bubbling H$_2$ through a stainless steel SiCl$_4$ bubbler at −4° C. The total flow of H$_2$ and SiCl$_4$ was 109 sccm, and the mole ratio of H$_2$ to SiCl$_4$ was 11.25:1. The gas and vapor leaving the bubbler was fed into the glass tube of a flow reactor containing the copper catalyst to form a silicon-containing copper catalyst. After 30 minutes the SiCl$_4$ flow was ceased, and a hydrogen flow of 100 sccm was maintained while cooling to 300° C. over a period of 1 hour. When the reactor reached 300° C., the H$_2$ was decreased to a flow rate of 5 sccm. H$_2$/CH$_2$Cl$_2$ was then fed through the reactor at a flow rate of 5 sccm, 300° C., and atmospheric pressure. The reaction was periodically sampled and analyzed by GC/GC-MS as described above to determine the Si-containing species leaving the reactor. Next, the H$_2$/CH$_2$Cl$_2$ feed was ceased, and the silicon-containing copper catalyst was activated/regenerated with 100 sccm H$_2$ at 600° C. It was then contacted again with H$_2$/SiCl$_4$, to reform the silicon-containing copper catalyst, for 30 min at 750° C. The combined flow rate of H$_2$ and SiCl$_4$ was 109 sccm, and the mole ratio of H$_2$ to SiCl$_4$ was 11.25:1. After the silicon-containing copper catalyst was reformed, it was purged with argon, again, and H$_2$/CH$_2$Cl$_2$ was contacted with the reformed silicon-containing copper catalyst as described above. This cycle was repeated once. The results are shown in Table 3. In Table 3, % in Effluent was calculated as in Example 2. This example demonstrates that silmethylenes are produced by the method of the invention and that the selectivity and production of chlorinated silamethylenes improves with subsequent cycles of catalyst regeneration and reaction.

TABLE 3

Production of halogenated organosilicon compounds, chloroethylenes, and chlorosilanes when silicon-containing copper catalyst is reacted with H$_2$/CH$_2$Cl$_2$.

| Cycle 1 | | Cycle 2 | |
|---|---|---|---|
| Compound | % in Effluent | Compound | % in Effluent |
| HCl | 13.68 | MeCl | 1.18 |
| MeCl | 4.66 | HSiCl$_3$ | 2.72 |
| HSiCl$_3$ | 0.71 | CH$_2$Cl$_2$ | 17.79 |
| CH$_2$Cl$_2$ | 63.94 | SiCl$_4$ | 4.17 |
| SiCl$_4$ | 8.17 | MeSiCl$_3$ | 8.96 |
| MeSiCl$_3$ | 1.50 | Me$_2$SiCl$_2$ | 0.39 |
| EtSiCl$_3$ | 0.09 | EtSiCl$_3$ | 0.56 |
| Cl$_3$SiCH$_2$SiCl$_3$ | 7.18 | Cl$_2$HSiCH$_2$SiHCl$_2$ | 2.74 |
| MeCl$_2$SiCH$_2$SiCl$_3$ | 0.06 | Cl$_2$HSiCH$_2$SiCl$_3$ | 22.11 |
| | | HCl$_2$SiCH$_2$SiCl$_2$Me | 3.60 |
| | | Cl$_3$SiCH$_2$SiCl$_3$ | 28.81 |
| | | MeCl$_2$SiCH$_2$SiCl$_3$ | 5.45 |
| | | Cl$_2$MeSiCH$_2$SiMeCl$_2$ | 0.70 |
| | | Cl$_3$Si(CH$_2$)$_2$SiCl$_3$ | 0.82 |

Cycle 1 main products were HCl, SiCl$_4$, and Cl$_3$SiCH$_2$SiCl$_3$.
Cycle 2 main products were Cl$_3$SiCH$_2$SiCl$_3$ and Cl$_2$HSiCH$_2$SiCl$_3$.

Example 4

CHCl₃ with Ar

Copper catalyst (0.75 g) comprising an activated carbon supported mixture of copper, gold, and magnesium, prepared as described above in example 1, was treated in $H_2$/$SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the glass tube of a flow reactor containing the copper catalyst to form a silicon-containing copper catalyst. After 30 minutes the $SiCl_4$ flow was ceased and a hydrogen flow of 100 sccm was maintained while cooling to 300° C. over a period of 1 hour. When the reactor reached 300° C., all $H_2$ was purged from the reactor and catalyst with an argon flow of 50 sccm for 30 min. After 30 min, the argon flow was ceased, and Ar/$CHCl_3$ was fed through the reactor at a flow rate of 5 sccm, 300° C., and atmospheric pressure. The reaction was periodically sampled and analyzed by GC/GC-MS as described above to determine the Si-containing species leaving the reactor. Next, the Ar/$CHCl_3$ feed was ceased, and the silicon-containing copper catalyst was activated/regenerated with 100 sccm $H_2$ at 600° C. It was then contacted again with $H_2$/$SiCl_4$, to reform the silicon-containing copper catalyst, for 30 min at 750° C. The combined flow rate of $H_2$ and $SiCl_4$ was 109 sccm, and the mole ratio of $H_2$ to $SiCl_4$ was 11.25:1. After the silicon-containing copper catalyst was reformed, it was purged with argon, again, and Ar/$CHCl_3$ was contacted with the reformed silicon-containing copper catalyst as described above. This cycle was repeated once. The results are shown in Table 4. In Table 4, % in Effluent was calculated as in Example 2. This example demonstrates that silmethylene chlorides can be produced by the method of the invention and that the selectivity and production of chlorinated silamethylenes improves with subsequent cycles of catalyst regeneration and reaction.

Example 5

CHCl₃ with H₂

Copper catalyst (0.75 g) comprising an activated carbon supported mixture of copper, gold, and magnesium, prepared as described above, was treated in $H_2$/$SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the glass tube of a flow reactor containing the copper catalyst to form a silicon-containing copper catalyst. After 30 minutes the $SiCl_4$ flow was ceased and a hydrogen flow of 100 sccm was maintained while cooling to 300° C. over a period of 1 hour. When the reactor reached 300° C., the $H_2$ was decreased to a flow rate of 5 sccm. $H_2$/$CHCl_3$ was then fed through the reactor at a flow rate of 5 sccm, 300° C., and atmospheric pressure. The reaction was periodically sampled and analyzed by GC/GC-MS as described above to determine the Si-containing species leaving the reactor. Next, the $H_2$/$CHCl_3$ feed was ceased, and the silicon-containing copper catalyst was activated/regenerated with 100 sccm $H_2$ at 600° C. It was then contacted again with $H_2$/$SiCl_4$, to reform the silicon-containing copper catalyst, for 30 min at 750° C. The combined flow rate of $H_2$ and $SiCl_4$ was 109 sccm, and the mole ratio of $H_2$ to $SiCl_4$ was 11.25:1. After the silicon-containing copper catalyst was reformed, the $H_2$/$CHCl_3$ was contacted with the reformed silicon-containing copper catalyst as described above. This cycle was repeated once. The results are shown in Table 5. In Table 5, % in Effluent was calculated as in Example 2. This example demonstrates that silamethylenes are produced by the method of the invention and that the selectivity and production of chlorinated silamethylenes improves with subsequent cycles of catalyst regeneration and reaction.

TABLE 4

Production of halogenated organosilicon compounds, chloroethylenes, and chlorosilanes when silicon-containing copper catalyst is reacted with Ar/$CHCl_3$.

| Cycle 1 | | Cycle 2 | |
| --- | --- | --- | --- |
| Compound | % in Effluent | Compound | % in Effluent |
| Argon | 19.67 | Argon | 11.85 |
| MeCl | 0.83 | $HSiCl_3$ | 14.46 |
| $HSiCl_3$ | 23.74 | $CH_2Cl_2$ | 2.84 |
| $CH_2Cl_2$ | 2.24 | $SiCl_4$ | 24.89 |
| $SiCl_4$ | 49.74 | $CHCl_3$ | 0.11 |
| $MeSiCl_3$ | 3.07 | $MeSiCl_3$ | 3.85 |
| $Cl_3SiCH_2SiCl_3$ | 0.70 | $ViSiCl_3$ | 0.37 |
| | | $EtSiCl_3$ | 0.07 |
| | | $Cl_2HSiCH_2SiCl_3$ | 3.80 |
| | | $Cl_3SiCH_2SiCl_3$ | 35.26 |
| | | $MeCl_2SiCH_2SiCl_3$ | 0.20 |
| | | $Cl_3Si(CH_2)_2SiCl_3$ | 2.30 |

TABLE 5

Production of halogenated organosilicon compounds, chloroethylenes, and chlorosilanes when silicon-containing copper catalyst is reacted with $H_2/CHCl_3$.

| Cycle 1 | | Cycle 2 | |
| --- | --- | --- | --- |
| Compound | % in Effluent | Compound | % in Effluent |
| HCl | 9.90 | HCl | 4.19 |
| MeCl | 0.96 | $HSiCl_3$ | 9.05 |
| $HSiCl_3$ | 7.68 | $CH_2Cl_2$ | 5.21 |
| $CH_2Cl_2$ | 2.99 | $SiCl_4$ | 23.54 |
| $SiCl_4$ | 33.67 | $CHCl_3$ | 18.53 |
| $MeSiCl_3$ | 2.19 | $MeSiCl_3$ | 4.38 |
| $Cl_3SiOSiCl_3$ | 0.43 | $ViSiCl_3$ | 0.39 |
| $Cl_3SiCH_2SiCl_3$ | 41.87 | $Cl_2HSiCH_2SiCl_3$ | 1.03 |
| $Cl_3Si(CH_2)_2SiCl_3$ | 0.31 | $Cl_3SiCH_2SiCl_3$ | 32.67 |
| | | $MeCl_2SiCH_2SiCl_3$ | 0.15 |
| | | $Cl_3Si(CH_2)_2SiCl_3$ | 0.47 |
| | | $EtCl_2SiCH_2SiCl_3$ | 0.40 |

Example 6

$CCl_4$ with Ar

Copper catalyst (0.75 g) comprising an activated carbon supported mixture of copper, gold, and magnesium, prepared as described above in example 1, was treated in $H_2/SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the glass tube of a flow reactor containing the copper catalyst to form a silicon-containing copper catalyst. After 30 minutes the $SiCl_4$ flow was ceased and a hydrogen flow of 100 sccm was maintained while cooling to 300° C. over a period of 1 hour. When the reactor reached 300° C., all $H_2$ was purged from the reactor and catalyst with an argon flow of 50 sccm for 30 min. After 30 min, the argon flow was ceased. Ar was then fed at 5 sccm through a bubbler containing $CCl_4$, and the bubbler effluent was fed through the reactor at 300° C. and atmospheric pressure. The reaction was periodically sampled and analyzed by GC/GC-MS as described above to determine the Si-containing species leaving the reactor. Next, the Ar/$CCl_4$ feed was ceased, and the silicon-containing copper catalyst was activated/regenerated with 100 sccm $H_2$ at 600° C. It was then contacted again with $H_2/SiCl_4$, to reform the silicon-containing copper catalyst, for 30 min at 750° C. The combined flow rate of $H_2$ and $SiCl_4$ was 109 sccm, and the mole ratio of $H_2$ to $SiCl_4$ was 11.25:1. After the silicon-containing copper catalyst was reformed, it was purged with argon, again, and Ar/$CCl_4$ was contacted with the reformed silicon-containing copper catalyst as described above. This cycle was repeated once. The results are shown in Table 6. In Table 6, % in Effluent was calculated as in Example 2. This example demonstrates that chlorinated silamethylenes are produced by the method of the invention and that the selectivity and production of chlorinated silamethylenes improves with subsequent cycles of catalyst regeneration and reaction.

TABLE 6

Production of halogenated organosilicon compounds, chloroethylenes, and chlorosilanes when silicon-containing copper catalyst is reacted with Ar/$CCl_4$.

| Cycle 1 | | Cycle 2 | |
| --- | --- | --- | --- |
| Compound | % in Effluent | Compound | % in Effluent |
| Argon | 18.32 | Argon | 17.59 |
| $SiCl_4$ | 6.96 | $HSiCl_3$ | 0.58 |
| $CCl_4$ | 69.19 | $SiCl_4$ | 41.07 |
| $Cl_2C=CCl_2$ | 2.75 | $Cl_3SiCH_2SiCl_3$ | 40.76 |
| hexachloroethane | 1.80 | | |
| $Cl_3SiCH_2SiCl_3$ | 0.97 | | |

Example 7

$CCl_4$ with $H_2$

Copper catalyst (0.75 g) comprising an activated carbon supported mixture of copper, gold, and magnesium, prepared as described above, was treated in $H_2/SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the glass tube of a flow reactor containing the copper catalyst to form a silicon-containing copper catalyst. After 30 minutes the $SiCl_4$ flow was ceased and a hydrogen flow of 100 sccm was maintained while cooling to 300° C. over a period of 1 hour. When the reactor reached 300° C., the $H_2$ was decreased to a flow rate of 5 sccm. $H_2/CCl_4$ was then fed through the reactor at a flow rate of 5 sccm, 300° C., and atmospheric pressure. The reaction was periodically sampled and analyzed by GC/GC-MS as described above to determine the Si-containing species leaving the reactor. Next, the $H_2/CCl_4$ feed was ceased, and the silicon-containing copper catalyst was activated/regenerated with 100 sccm $H_2$ at 600° C. It was then contacted again with $H_2/SiCl_4$, to reform the silicon-containing copper catalyst, for 30 min at 750° C. The combined flow rate of $H_2$ and SiCl$_4$ was 109 sccm, and the mole ratio of H$_2$ to SiCl$_4$ was 11.25:1. After the silicon-containing copper catalyst was reformed, the H$_2$/CCl$_4$ was contacted with the reformed silicon-containing copper catalyst as described above. This cycle was repeated once. The results are shown in Table 7. In Table 7, % in Effluent was calculated as in Example 2. This example demonstrates that chlorinated silaalkylenes are produced by the method of the invention and that the selectivity and production of chlorinated silaalkylenes improves with subsequent cycles of catalyst regeneration and reaction.

Table 7. Production of halogenated organosilicon compounds, chloroethylenes, and chlorosilanes when silicon-containing copper catalyst is reacted with H$_2$/CCl$_4$.

TABLE 7

Production of halogenated organosilicon compounds, chloroethylenes, and chlorosilanes when silicon-containing copper catalyst is reacted with H$_2$/CCl$_4$.

| Cycle 1 | | Cycle 2 | |
| --- | --- | --- | --- |
| Compound | % in Effluent | Compound | % in Effluent |
| HCl | 12.69 | HCl | 8.38 |
| HSiCl$_3$ | 1.33 | HSiCl$_3$ | 4.16 |
| SiCl$_4$ | 19.72 | SiCl$_4$ | 26.22 |
| CHCl$_3$ | 4.33 | CHCl$_3$ | 4.29 |
| CCl$_4$ | 25.44 | CCl$_4$ | 17.02 |
| Cl$_2$C=CHCl | 1.14 | Cl$_2$C=CHCl | 1.57 |
| Cl$_2$C=CCl$_2$ | 8.33 | Cl$_2$C=CCl$_2$ | 8.01 |
| Cl$_3$SiCH$_2$SiCl$_3$ | 27.01 | Cl$_3$SiCH$_2$SiCl$_3$ | 29.26 |
| | | Cl$_3$Si(CH$_2$)$_2$SiCl$_3$ | 1.09 |

The invention claimed is:

1. A method comprises separate and consecutive steps (i) and (ii), where
   Step (i) comprises contacting a copper catalyst with hydrogen gas and a halogenated silane monomer at a temperature of 500° C. to 1400° C. to form a silicon-containing copper catalyst comprising at least 0.1% (w/w) of silicon; and
   Step (ii) comprises contacting the silicon-containing copper catalyst with an organohalide at a temperature of 100° C. to 600° C. to form a reaction product comprising a halogenated silahydrocarbylene, where the organohalide has formula H$_a$C$_b$X$_c$, where X is a halogen atom, subscript a is an integer of 0 or more, subscript b is an integer of 1 or more, and subscript c is an integer of 2 or more.

2. The method of claim 1, where the copper catalyst further comprises at least one element selected from calcium, cesium, gold, magnesium, nickel, sulfur, tin, and zinc.

3. The method of claim 1, where the halogenated silane monomer comprises a monomer selected from a silicon tetrahalide, a trihalosilane, and a combination thereof.

4. The method of claim 1, further comprising a third step (iii) in which the separate and consecutive first step (i) and second step (ii) are repeated one or more times.

5. The method of claim 1, further comprising purging the silicon-containing copper catalyst formed in step (i) with at least one of hydrogen gas and an inert gas before contacting the silicon-containing copper catalyst with the organohalide in step (ii).

6. The method of claim 5, where the silicon-containing copper catalyst is first purged with hydrogen gas and then subsequently purged with an inert gas.

7. The method of claim 1, where the copper catalyst further comprises a metal oxide or carbon-based support.

8. The method of claim 1, where the copper catalyst comprises copper, gold, and magnesium.

9. The method of claim 1, where a mole ratio of hydrogen gas to halogenated silane monomer is from 15:1 to 1:1.

10. The method of claim 1, where the organohalide is selected from: 1) an alkyl halide where subscript b is 1 to 10, and 2) a cycloalkyl halide where subscript b is 4 to 10.

11. The method of claim 10, where the organohalide is an alkyl halide, subscript b is 1, subscript c is 2, 3, or 4, and each X is Cl.

12. The method of claim 1, where the halogenated silahydrocarbylene has formula X$_d$H$_e$R$^1_f$Si—R—SiX$_d$H$_e$R$^1_f$, where each X is independently a halogen atom; each subscript d is independently 0, 1, 2, or 3, with the proviso that at least one instance of d>0; each subscript e is independently 0, 1, or 2; each subscript f is independently 0, 1, or 2; with the proviso that a quantity (d+e+f)=3, each R$^1$ is independently a monovalent hydrocarbon group, and R is a divalent hydrocarbon group.

13. The method of claim 1 further comprising the step of recovering the halogenated silahydrocarbylene.

14. The method of claim 1, where the temperature at which the reactants in step (i) contact the copper catalyst is 500° C. to 950° C.

15. The method of claim 1, where the method further comprises step (iv): forming a resin from the halogenated silahydrocarbylene.

* * * * *